(12) United States Patent
Fisher et al.

(10) Patent No.: US 8,152,301 B2
(45) Date of Patent: Apr. 10, 2012

(54) VISION TESTING SYSTEM AND METHOD

(75) Inventors: Scott Warren Fisher, Flagstaff Hill (AU); Warwick Freeland, Somerton Park (AU)

(73) Assignee: Carl Zeiss Vision Australia Holdings Limited, Lonsdale, South Australia ( * ) Notice: Subject to any disclaimer, the term of this patent is extended or adjusted under 35 U.S.C. 154(b) by 656 days.

(21) Appl. No.: 12/093,542

(22) PCT Filed: Nov. 15, 2006

(86) PCT No.: PCT/AU2006/001696
§ 371 (c)(1),
(2), (4) Date: Jul. 9, 2008

(87) PCT Pub. No.: WO2007/056796
PCT Pub. Date: May 24, 2007

(65) Prior Publication Data
US 2008/0309880 A1    Dec. 18, 2008

(30) Foreign Application Priority Data
Nov. 15, 2005 (AU) ................................ 2005906336

(51) Int. Cl.
*A61B 3/00* (2006.01)
*A61B 3/02* (2006.01)
(52) U.S. Cl. ........................................ 351/246; 351/239

(58) Field of Classification Search .................. 351/239, 351/246
See application file for complete search history.

(56) References Cited

U.S. PATENT DOCUMENTS
4,726,672 A    2/1988    O'Brien et al.

FOREIGN PATENT DOCUMENTS
| JP | 2003-284867 A | 10/2003 |
| WO | WO 92/00037 A1 | 1/1992 |
| WO | WO 2004/038542 A2 | 5/2004 |
| WO | WO 2004/089199 A1 | 10/2004 |

OTHER PUBLICATIONS
Form PCT/ISA/210 (International Search Report) dated Feb. 16, 2007.

*Primary Examiner* — Jack Dinh
(74) *Attorney, Agent, or Firm* — Buchanan Ingersoll & Rooney PC (57) ABSTRACT

A method for testing a person's vision is disclosed. The method includes providing, for display to the person, one or more sequences of test images, each test image including one or more test symbols. For each test image, a target symbol is identified to the person. The person then views each test image in the sequence and activates a control in response to recognizing a test symbol that replicates the shape of the target symbol. At the completion of the sequence, a parameter value associated with the activations is processed and correlated with a vision metric. A system for testing a person's vision is also disclosed.

22 Claims, 10 Drawing Sheets

| SIZE | | | VISION METRIC | |
|---|---|---|---|---|
| MAR | logMAR | DECIMAL | METRIC | IMPERIAL |
| 10 | 1 | 0.1 | 6/60 | 20/200 |
| 8 | 0.9 | 0.13 | 6/48 | 20/160 |
| 6.3 | 0.8 | 0.16 | 6/38 | 20/125 |
| 5 | 0.7 | 0.2 | 6/30 | 20/100 |
| 4 | 0.6 | 0.25 | 6/24 | 20/80 |
| 3.2 | 0.5 | 0.32 | 6/19 | 20/60 |
| 2.5 | 0.4 | 0.4 | 6/15 | 20/50 |
| 2 | 0.3 | 0.5 | 6/12 | 20/40 |
| 1.6 | 0.2 | 0.63 | 6/9.5 | 20/30 |
| 1.25 | 0.1 | 0.8 | 6/7.5 | 20/25 |
| 1 | 0 | 1 | 6/6 | 20/20 |
| 0.8 | -0.1 | 1.25 | 6/4.8 | 20/16 |
| 0.63 | -0.2 | 1.58 | 6/3.8 | 20/12.5 |
| 0.5 | -0.3 | 2 | 6/3.0 | 20/10 |

FIG.8

| logMAR | METRIC |
|---|---|
| ≥0.1 | EXCELLENT |
| 0.1≤ to ≥ -0.1 | ACCEPTABLE |
| ≥0-.1 | POOR |

VISION TESTING SYSTEM AND METHOD

This application claims priority from Australian Provisional Patent Application No. 2005906336 filed on 15 Nov. 2005, the contents of which are to be taken as incorporated herein by this reference.

FIELD OF THE INVENTION

The present invention relates to vision testing. In a typical application, the present invention may be used to assess a person's visual acuity.

BACKGROUND OF THE INVENTION

Conventional vision testing involves reading charts, looking at light sources, or making decisions as to where or what highly simplified stimuli are. Such test methods are often tedious, requiring the person to make repeated determinations of the clarity of a viewing condition, or to identify symbols. The process is often conducted under well controlled but restrictive conditions. Consequently, practitioners can find it difficult to maintain the attention of children in these conditions, impacting on the validity of the results.

In view of the above, existing test methods may not appeal to the person undergoing the test, especially juvenile persons. The present invention seeks to provide a vision testing method and system that is more engaging for the person.

SUMMARY OF THE INVENTION

The present invention provides a method of testing a person's vision, the method including: displaying one or more sequences of test images, each test image including one or more test symbols; for each test image, or for each sequence, identifying a target symbol to the person; the person viewing each test image in the sequence and activating a control in response to recognising a test symbol that replicates the shape of the target symbol; processing activation information associated with the activation of the control to obtain a parameter value associated with the activations; and correlating the parameter value with a vision metric.

A method in accordance with an embodiment of the present invention will typically be conducted in a computer generated environment, such as a computer game like environment. Such an environment is expected to be more engaging for the person undergoing the test, particularly for young children or juveniles. However, other environments which are not computer game like, but which are also configured to engage with the person, may also be used. For example, an embodiment may be conducted in a computer generated environment that creates a 'theme' based experience for the person. In one embodiment, the person may select a theme that provides a sequence of test images relating to a sport based theme, in which case the test symbols may include sports based icons.

A computer generated environment is also expected to offer additional advantages. For example, a computer based test may allow the test to be conducted over a computer network, such as the Internet. For example, in one embodiment the test may be accessible to the person by activating, at a client computer, an address that links the client computer to a server hosting a computer program containing instructions that are executable by the client, or the server, to conduct the test.

In one embodiment, a person's vision is tested in terms of their visual acuity. However, other embodiments may test different aspects of a person's vision, such as one or more of near vision acuity, distance vision acuity, contrast sensitivity, stereo-acuity, binocular function, and peripheral vision performance.

Typically, the sequence of test images will be displayed on, or by, a graphics display device having suitable display characteristics such as a liquid crystal device (LCD) display device, a plasma display device, a cathode ray tube (CRT) based display device or a data projector. A suitable display will be capable of displaying test images with the addition of no, or at least a minimal amount of, visible artefacts to the test symbols, at least over a range of test symbol sizes, so as to not effect the test outcome.

The sequence of test images may be displayed as a sequence of dynamic test images in the sense that each test image may include moving image features, including moving test symbols, and thus be dynamic in nature. Alternatively, the sequence may include a sequence of static test images that, when displayed in the sequence, form a dynamic sequence of images in the sense that consecutive test images contain different image features. Thus, throughout this specification references to the term "dynamic", when used to describe an image or a sequence of test images, are to be understood as a reference to an image, or a sequence of images, that changes in appearance over time such that the image, or the sequence of images, involves motion or movement of image features either in the image or in the sequence of images.

In one embodiment, each test image is a dynamic image that spans a particular test interval of a sequence. In such an embodiment, and by way of example, each test image may include a video or animated image spanning a test interval with a duration defined by start time and an end time. In such a case, the sequence of test images may include a sequence of test images wherein each test image comprises a discrete video or animated image and wherein the duration of the sequence is the sum of the test intervals for the test images comprising the sequence.

Although an embodiment of the present invention may use dynamic test images including, for example, a video or animated image, a method in accordance with another embodiment may use a sequence of test images in the form of a sequence of static test images, arranged such that consecutive test images are different. In other words, in such an embodiment, consecutive test images in the sequence may be different so that the sequence itself is dynamic in nature.

The test symbols may have any suitable form and may include for example, numbers, letters, signs, icons or other visual representations. In an embodiment, each test symbol is an optotype.

The target symbol will typically be a selected from one of a range of displayable test symbols and will typically be identified to the person on the same display displaying the sequence of test images. It will of course be appreciated that the target symbol may be identified to the person in other ways including, for example, using an audio cue that identifies the target symbol. The target symbol may be the same for each test image or each sequence of test images, or it may be different.

In one embodiment, the sequence of test images is arranged to include one or more test symbols having a size that progressively enlarge during a test interval. Thus, the present invention also provides a method of testing a person's vision, the method including: providing a test image including a test symbol having a size that, during a test interval, progressively enlarges from an size at which the symbol is unrecognisable to the person to a size at which the symbol is recognisable to the person; the person activating a control at the instant, during the test interval, that the person recognises the symbol; and correlating the size of the test symbol, at the time of activation, with a vision metric.

Although an embodiment of the present invention relies on size information (such as angular size information) for the test symbols in order to obtain a test result, a skilled person will appreciate that the present invention may be configured to conduct vision tests which utilise, or vary, other characteristics of the test symbols.

In an embodiment, only some of the test images include a test symbol that replicates the shape of the target symbol, whereas other test images in the may include a test symbol that is different to the target symbol. Accordingly, it is not essential that each test image include a test symbol having a shape that replicates the shape of the target symbol.

In an embodiment that includes test images that include a test symbol that progressively enlarges during a test interval, the person will typically activate the control at the instant, during the test interval, that the person recognises the test symbol as having a shape that replicates the target symbol. In other words, the person will activate the control at the instant that the angular size of the test symbol, or the angular size of the features of the test symbol, is such that the person can discriminate that the test symbol has a shape, or spatial pattern, that replicates that of the target symbol.

In another embodiment, in which the sequence of test images includes a set of static test images, consecutive test images may differ in response to the activation of the control by the person. For example, in one embodiment the size of the one or more test symbols included in each test image may differ between consecutive test images such that a first test image may include a set of test symbols of a first size and a consecutive test image including a set of test symbols of a smaller or larger size. For example, in one embodiment the person is required to activate the control on recognising a selected one of the test symbols as replicating the shape of the target symbol. If the activation of the control by the person is indicative of the person correctly recognising, and thus correctly discriminating, the test symbol replicating the shape of the target symbol, then the next test image in the sequence may include a set of test symbols having a smaller size than the test symbols of the first test image, with the general idea being that the size of the test symbols will continue to reduce in size for further test images in the sequence in response to the person correctly recognises the test symbol replicating the shape of the target symbol. On the other hand, if the activation of the control by the person is indicative of the person not recognising, and thus incorrectly discriminating the test symbol replicating the shape of the target symbol from the other displayed test symbols, then the next test image in the sequence may include a set of test symbols having a larger size than the first test image. Thus, in one embodiment, irrespective of whether the person correctly or incorrectly activates the control, consecutive test images will differ in response to the activation of the control by the person.

For the remainder of the description, an activation that is indicative of the person correctly recognising a test symbol replicating the shape of the target symbol will herein be referred to as a 'correct activation', whereas an activation that is indicative of the person incorrectly recognising a test symbol will be referred to as an 'incorrect activation'.

The activation of the control may include the person activating any suitable control. For example, the control may include, for example, an input device such as a touch screen interface overlayed onto the display, a mouse, a trackball, a joystick control, a wireless switch, a microphone, a keyboard, a keypad, a touch pad, a button, a motion sensing device, or another suitable input device. Typically, the control will be configured to communicate with a processor running a computer software program for providing the sequence of test images, processing the processing a parameter value associated with the activations and correlating the parameter value with a vision metric.

The sequence of test images may terminate in response to detecting a specified threshold value indicative of the degree to which the person is able to reliably correctly recognise test symbols, of a particular size, that replicate the shape of the target symbol. Typically, the threshold will be a minimum threshold value indicative of the reliability at which the person can recognise a particular size of the test symbols. Typically, the minimum threshold value will be for the smallest size test symbol that the person can reliably recognise at that threshold value.

The minimum threshold value may include a predefined threshold value, expressed as a percentage, such as for example, a 50%, 75% or 95% correct performance threshold level for a particular target symbol.

In one embodiment, a parametric estimation by sequential testing staircase procedure is be used with a 75% threshold value. In such an embodiment, for consecutive static test images including one or more test symbols, the size of the test symbol replicating the target symbol may be increased or decreased until a 75% correct threshold value is achieved, at which point the sequence, and thus the test, is terminated.

Although in one embodiment the sequence of test images may terminate in response to detecting a particular threshold value, this need not be the case in all embodiments. For example, in another embodiment, the sequence may terminate at the end of a pre-specified duration, or after the display of a specified number of test images.

In terms of processing activation information, such information may include information that is indicative of the size of the test symbol at the instant the control was activated, information relating to response times, information identifying the group or type of test symbol for each correct activation, or information identifying the activation accuracy of the person in terms of a ratio that expresses the number of times they have correctly recognised test symbols of different sizes against the number of times test symbols of that size have been displayed.

The size may be expressed in terms of a minimum angle of resolution (MAR) or derivatives of the MAR, such as a logarithmic (LogMAR) derivative or a decimal derivative. As will be appreciated, the minimum angle of resolution equals the visual angle (usually expressed in minutes of arc) subtended by a test symbol, or features of a test symbol, at the person's eye In one embodiment processing the activation information includes processing size information for each of the test symbols associated with correct activations to obtain a parameter in the form of a statistical value based on the size of those test symbols. For example, in an embodiment in which the test symbols progressively enlarge from a size at which the test symbol is unrecognisable to the person to a size at which the test symbol is recognisable to the person, processing a parameter value associated with the activations may include processing size information for each of the test symbols associated with correct activations at the respective instants when the control was activated to calculate a statistical value derived for the size information. In such an embodiment, processing activation information may also take into account incorrect activations.

Any suitable statistical value may be used, including for example, the mean, the median, or the standard deviation of the size of the test symbols associated with activations. In this respect, the size of the test symbols may be expressed dimensionally (for example, in terms of the height and width characteristics), or in terms of the angular resolution of the test symbols for a specified distance from the display as MAR, LogMAR, or a decimal equivalent of MAR.

Although one embodiment uses one or more statistical values derived from the size of the test symbols associated with correct activations, it will be appreciated that other parameters, or indeed other combinations of parameters, may be similarly used, including, for example, the activation time (in other words, the time the person takes to recognise a test symbol that replicates the target symbol). For example, in one embodiment, correlating the value of the activation parameter with a vision metric includes correlating the elapsed time at which the control was activated, relative to the time at which a test image was first displayed to the person.

In one embodiment, correlating the parameter value with a vision metric may include obtaining a value for a metric of visual acuity having a predetermined relationship with the average size of the test symbols associated with the correct activations. In such an embodiment, obtaining a value for a metric of visual acuity may involve retrieving, from a scale of values, a value having a predetermined relationship with the value of the average size. However, it will be appreciated that such a scale could also be used for other types of statistical values. Correlating the parameter value with the vision metric may be performed by the processor. Alternatively, the processor may output the parameter value for use by a user to retrieve a value of a vision metric manually, such as from a chart or table.

In another embodiment, the statical value is the smallest size of the test symbols that the person is able to detect at a ratio that exceeds the correct threshold value. In such an embodiment, obtaining a value for a metric of visual acuity may involve retrieving, from a scale of values, a value having a predetermined relationship with the value of the minimum size value.

The scale may be expressed in any suitable form. One suitable scale may express a qualitative relationship between visual acuity and the statistical value. For example, the scale may express, for different respective bands of average sizes, visual acuity as "good", "satisfactory", or "poor", or the like. Another suitable scale may express the predetermined relationship between visual acuity and average size quantitatively using, for example, a conventional quantitative metric of visual acuity.

In an embodiment, a vision metric score is provided to the person at the completion of the test interval.

The present invention also provides an interactive system for testing the vision of a person, the system including: a graphics display device; a graphics processor for providing, for display on the graphics display device, a sequence of test images, each test image including one or more test symbols; an identifying means for identifying, for each test image or sequence, a target symbol to the person; a controller that is activatable by the person viewing each test image in the sequence in response to recognising a test symbol that replicates the shape of the target symbol; a processor for: processing activation information to obtain a value for an activation parameter for correlation with a vision metric.

In one system in accordance with an embodiment of the present invention, each test image in the sequence of test images is in the form of a dynamic graphical image that spans a test interval and that includes a test symbol that progressively enlarges during a test interval. In such an embodiment, the symbol enlarges from a size at which the symbol is unrecognisable to the person to a size at which the symbol is recognisable to the person. Thus the present invention also provides an interactive system for testing the vision of a person, including: a graphical display device; a graphics processor for providing, on the graphical display device, a dynamic graphical image including a test symbol that progressively enlarges during a test interval, the test symbol enlarging from a size at which the symbol is unrecognisable to the person to a size at which the symbol is recognisable to the person; a control means for activation at the instant, during the test interval, that the person recognises the symbol on the display; and a processor for correlating the activation of the control with a vision metric.

In an embodiment, the interactive system is in the form of a computer game.

The present invention is expected to find application in vision screening of the type that is traditionally conducted using Landolt ring type testing, a Lea test, or a Snellen chart. However, it is envisaged that the present invention will provide a test that is expected to be more engaging, particularly for young children or juveniles.

BRIEF DESCRIPTION OF THE DRAWINGS

The present invention will now be described in relation to a preferred embodiment as illustrated in the accompanying drawings. However, it must be appreciated that the matter illustrated presents only one technique for embodying the invention. Other configurations and arrangements are envisaged as also being within the scope of the invention as generally described above.

In the drawings.

DETAILED DESCRIPTION OF EMBODIMENTS

In the following description, it will be convenient to describe various embodiments of the invention by reference to various applications which relates to testing a person's visual acuity. However, it is envisaged that the proposed method of testing a person's vision will be applicable to a broad range of visual tests, such as stereopsis test, contrast sensitivity test, fixation disparity, muscular balance, and colour vision.

Figure 1:
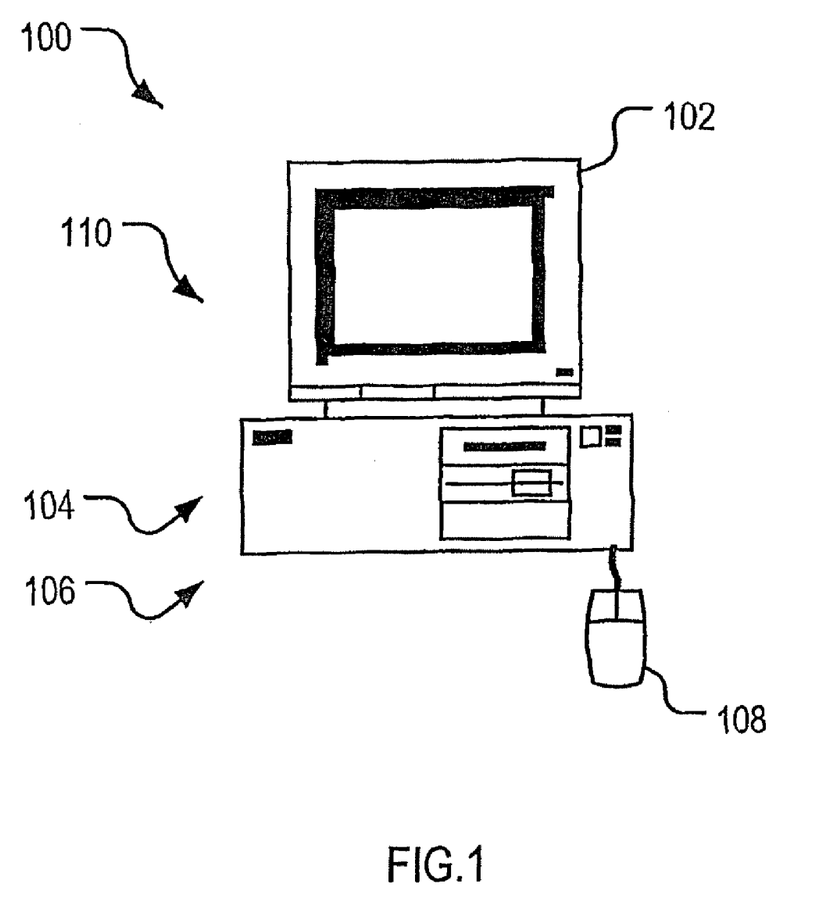
FIG. 1 is a simplified block diagram of a system according to an embodiment of the present invention.

Referring firstly to FIG. 1, there is shown a simplified block diagram of an example system 100 for conducting a visual test according to an embodiment of the present invention. In the depicted embodiment, hardware elements of the system 100 include a display device 102, a graphics processor 104, a processor 106 and a control 108 (shown here as a mouse).

In the illustrated embodiment the system 100 includes as a desk-top computer 110, such as an IBM compatible desktop computer equipped with program memory storing application computer software that is executable by the processor 106 of the computer 110 to provide an application environment for conducting the method. Designing suitable computer software for conducting the method would be within the capabilities of a skilled computer programmer.

In the present case, since the system 100 includes a desktop computer 110, the graphics processor 104 and the processor 106 are included as modules of that computer. For example, the processor 106 will be installed on a mother board component of the computer 110, and the graphics processor will be installed on a graphics card component of the computer 110. It will of course be appreciated that other types of computers will be suitable for use in a system embodiment. For example, a laptop computer, a handheld computer, or a custom designed computer may also be suitable. In addition, the system 100 may be implemented using hardware, software or a combination thereof and may be implemented in one or more computer systems or processing systems. Indeed, the functionality of the system 100 may be provided by one or more computer systems.

In the illustrated embodiment, the display device 102 includes a graphics display device that is compatible with the computer 110. In an embodiment, the display device 102 includes a 17" LCD monitor providing an 8 ms response time, a brightness of 300cd/m$^2$ and a contrast ratio of 450:1. However it will be appreciated that other display device configurations, providing different technical specifications, may be used in other embodiments. For example, the display device 102 may include a conventional cathode ray display (CRT), a display projector (such as a DLP DDR projector), or a head mounted display device.

As will be explained in more detail later, although the configuration and technical specifications of suitable display devices 102 may vary, it is important that the display device 102 be capable of resolving specified features of test symbols generated during the test without introducing visible artefacts that may otherwise adversely affect the accuracy of the test outcomes, at least for a range of test symbol sizes.

Figure 2:
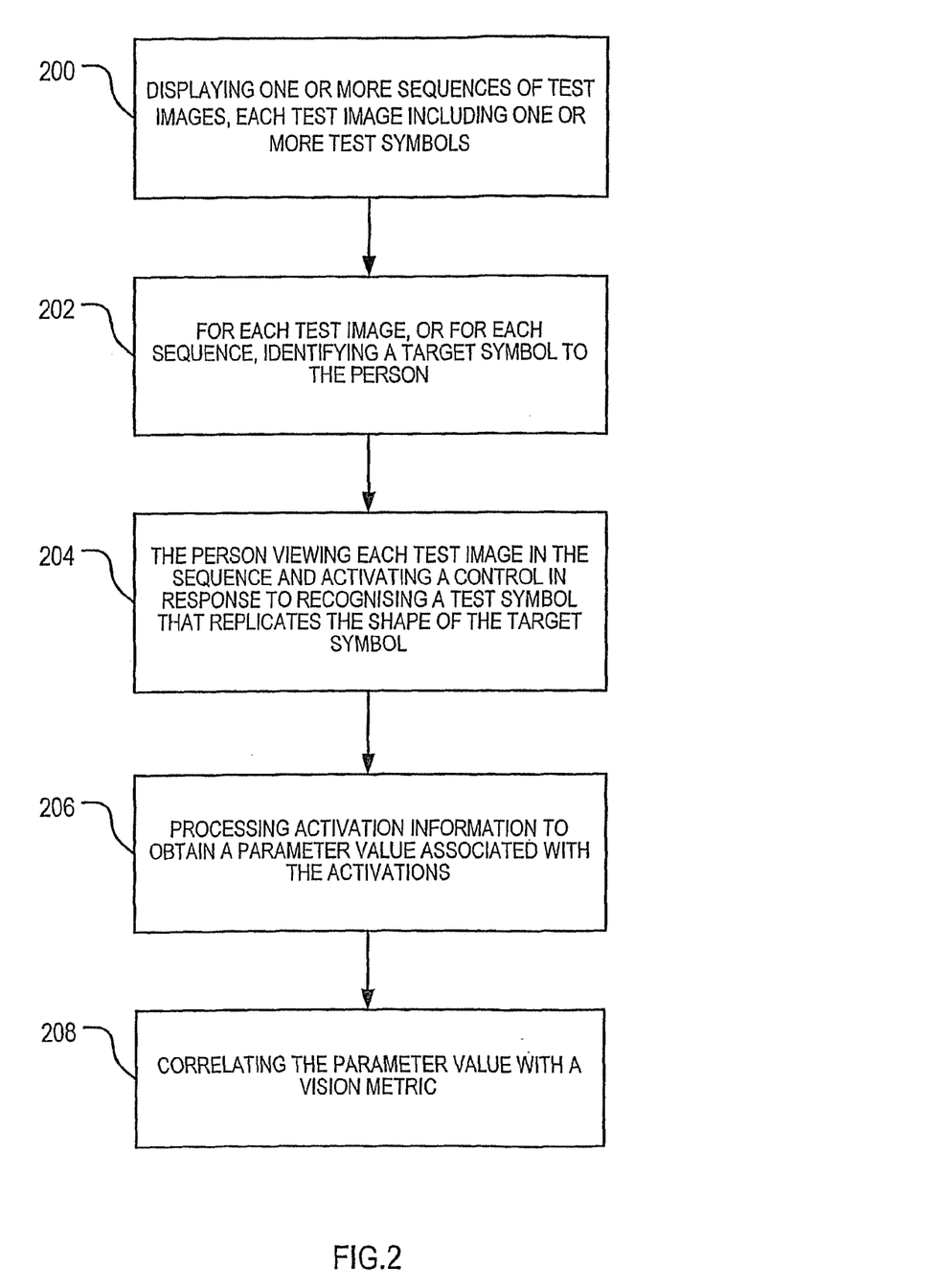
FIG. 2 is a flow diagram of a visual test method in accordance with an embodiment of the present invention.

Referring now to FIG. 2, at step 200 the graphics processor 104 (ref. FIG. 1) provides, on the graphical display device 102 (ref. FIG. 1), a display comprising a sequence of test images, such that each test image includes one or more test symbols. At step 202, for each test image, or for each sequence, a target symbol is also displayed, and thus identified to the person undergoing the test.

At step 204, the person views each test image in the sequence and activates the control 108 (ref. FIG. 1) in response to recognising a test symbol that replicates the shape of the target symbol. At step 206, the processor 106 processes activation information to obtain a parameter value associated with the activations and then, at step 208, correlates the parameter value with a vision metric expressing the test result.

Various examples of different methods for conducting a visual test in accordance with different embodiments of the present invention will now be described to assist the reader in understanding the present invention.

Example 1

Figure 3:
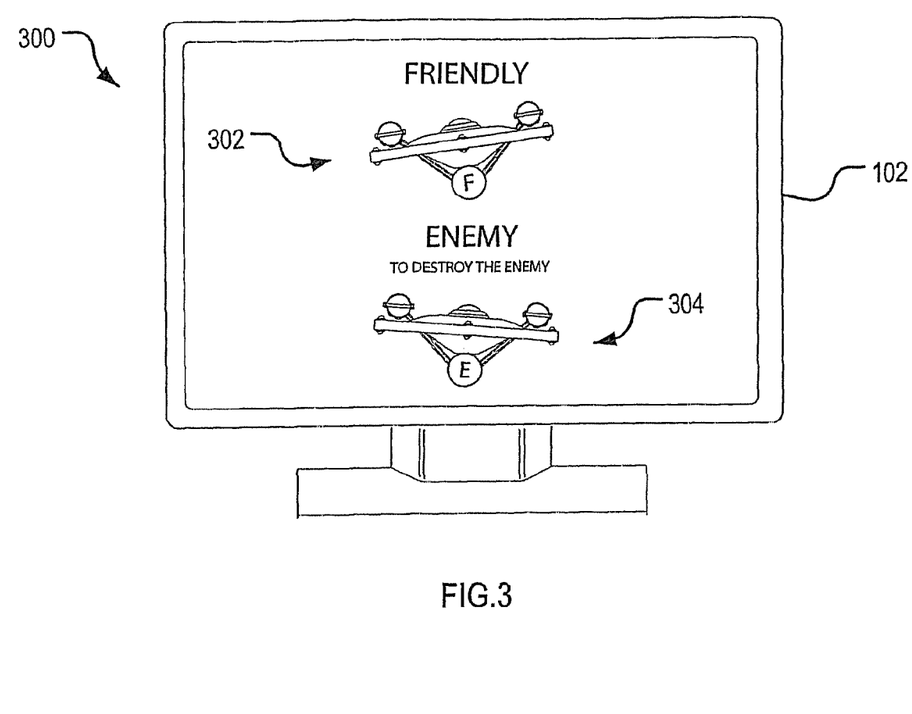
FIG. 3 is an example of a pair of test symbols for use with the system of FIG. 1.
Figure 4:
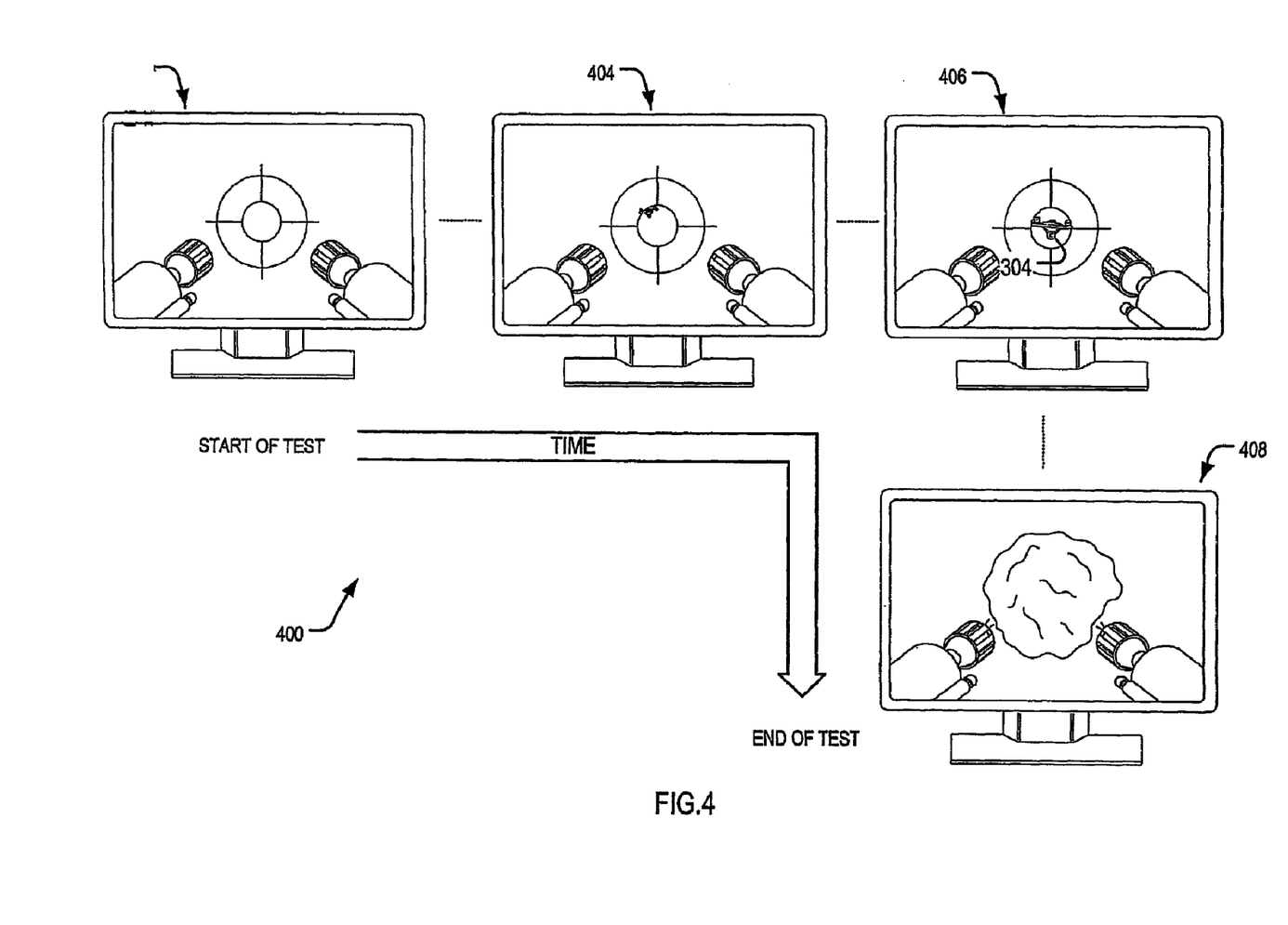
FIG. 4 is an example sequence of test images for a method embodiment of the present invention.
Figure 5:
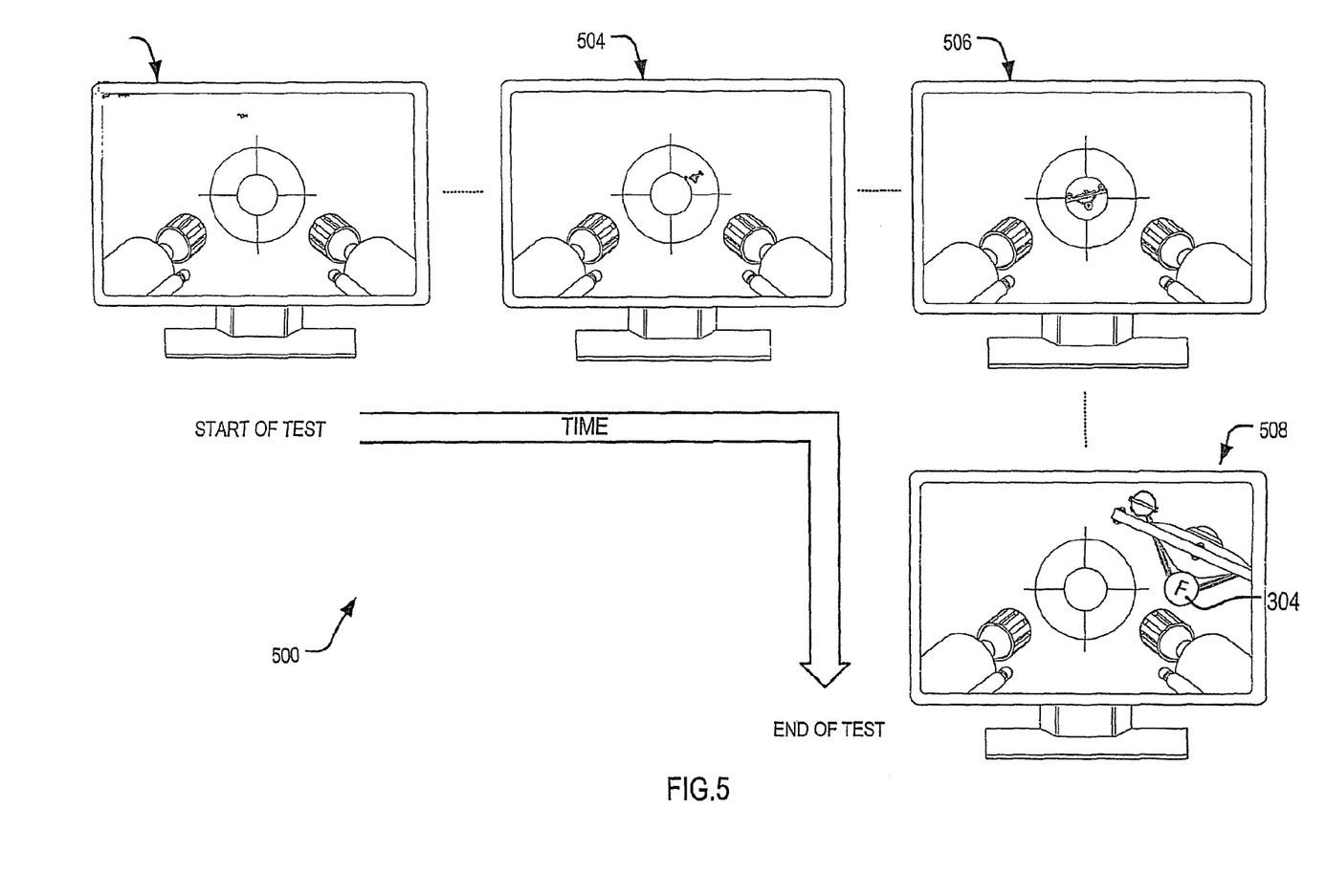
FIG. 5 is another example sequence of test images for the method embodiment shown in FIG. 4.

FIG. 3 to FIG. 5 relate to an example of an embodiment of the present invention that displays a sequence of test images such that each test image includes a single test symbol that enlarges over the duration of the sequence. In the present case, each test symbol enlarges incrementally over a range of sizes.

Referring firstly to FIG. 3, prior to commencement of the test, a pair of image elements (shown here as images of a space craft) including test symbols 302, 304 are displayed to the person undergoing the test. In this example, the pair of test symbols 302, 304 includes an "F" symbol 302 and an "E" symbol 304. Typically, the test symbols 302, 304 will be optotypes, however for clarity purposes they have not been depicted as such in FIG. 3 to FIG. 5.

In the present case, each test symbol 302, 304 is associated with a respective image element (in this, an image of a "space ship") to add further interest to the test. It is not essential that the test symbols 302, 304 be associated with a respective image element.

One of the test symbols 302, 304 is identified to the person undergoing the test as a target symbol (shown labelled as 'friendly'). During the test, the person views a sequence of test images and activates the control means 108 (ref. FIG. 1) upon recognising, in the sequence of test images, a test symbol that replicates the shape of the target symbol. Thus, in the present case, the person is instructed to activate the control means 108 (ref. FIG. 1) on recognising the "E" symbol 204, which will typically occur when the test symbol 204 has a size which is sufficiently large for the person to discriminate the features of the test symbol, and thus recognise a test symbol as having a shape that replicates that of the target symbol 204.

FIG. 4 and FIG. 5 show different example sequences of test images for a test in accordance with the first embodiment.

Referring to FIG. 4 there is shown a sequence 400 of test images 402, 404, 406, 408 for a test in which an "E" symbol 302 is progressively enlarged, during a test interval, from a size at which the symbol is unrecognisable to the person to a size at which the symbol is recognisable to the person. As shown, the environment in which the test is conducted resembles a computer game. Indeed, in the present case the activation of the control means 108 (ref. FIG. 1) triggers a graphical representation of a cannon firing at the image element associated with a test symbol 302.

In the example sequence shown in FIG. 4, the person has activated the control 108 (ref. FIG. 1) in response to recognising the test symbol at the size displayed in test image 406. However, it will be appreciated that the test images 402, 404, 406, 408 shown in FIG. 3 are shown for illustrative purposes only. Typically, the sequence 400 will include additional test images located between the test images 402, 404, 406, 408. In the illustrated example such additional test images have been omitted for clarity.

Turning now to FIG. 5 there is shown an example sequence 500 of test images 502, 504, 506, 508 for a test interval in which an "F" symbol 304 is progressively enlarged, during the test interval, from a size at which the test symbol 304 is unrecognisable to the person to a size at which the test symbol 304 is recognisable to the person. In the present case, the "F" symbol 304 is a test symbol that, on recognition by the person, does not require activation of the control means 108 since it does replicate the shape of the target symbol.

An example sequence of the type depicted in FIG. 5 may be included in a test so as to provide a mechanism for detecting when a person is not properly conducting the test. For example, activation information for incorrect activations may processed to establish that the person is attempting to defeat the purpose of the test, or manipulate the test outcome.

At the completion of the test, which will typically include multiple sequences, activation information is processed to obtain a parameter value which is then correlated with a vision metric. In the present case, the activation information includes average size information for the test symbols associated with correct activations. Correlating the average size with a vision metric includes indexing the size information into a look-up table containing a vision metric for a range of average sizes. However, it will be appreciated that other types of activation information may be used.

The correlation of the activation information with the vision metric may also take into account any activation of the control means 108 in response to an incorrect activation. In other words, the person activating the control means 108 in response an incorrectly activation of the control 108.

Example 2

Figure 6:
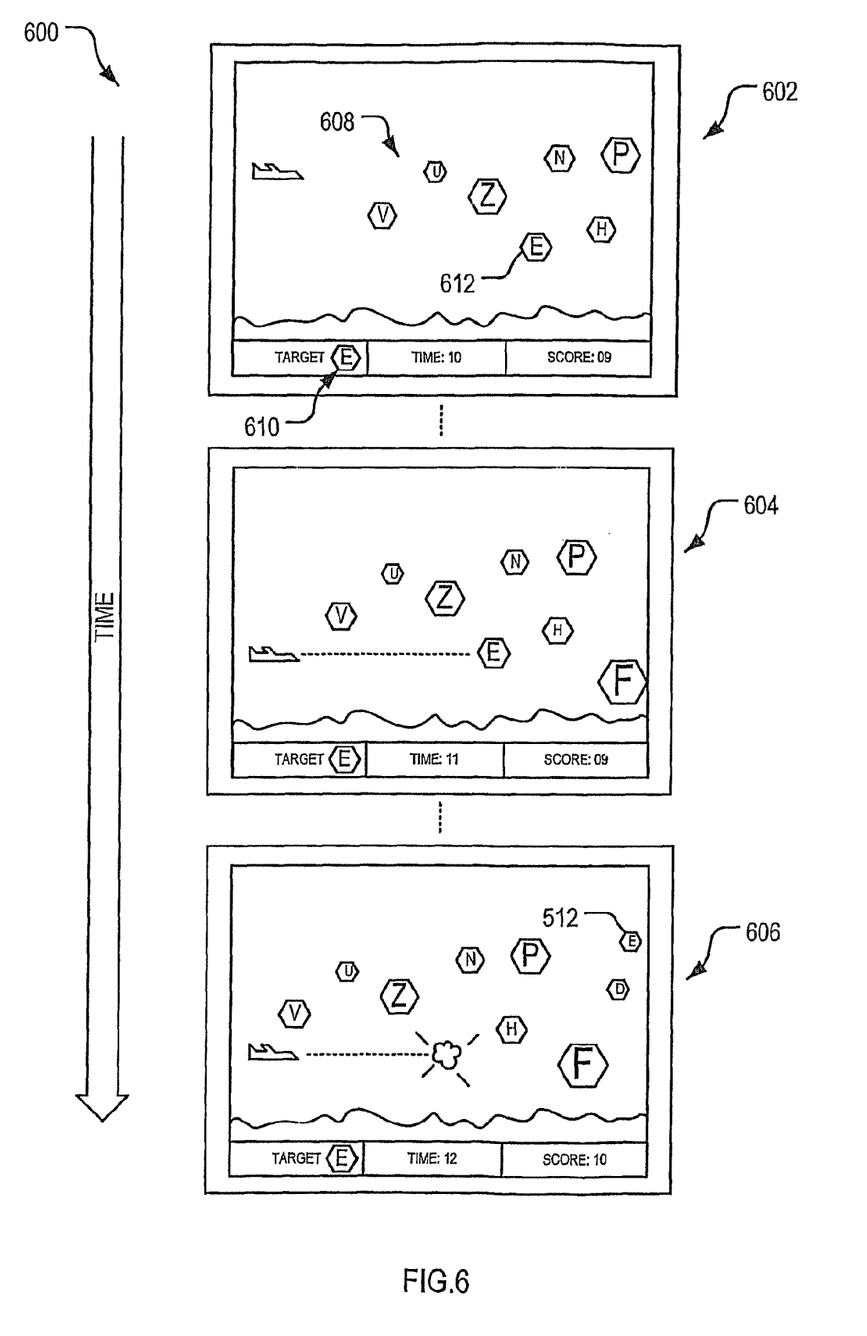
FIG. 6 is an example of a sequence of test images for a method in accordance with a second embodiment of the present invention.

Referring now to FIG. 6 there is shown an example sequence 600 of test images 602, 604, 606 for a test method in accordance with a second embodiment of the present invention.

In this example, each test image 602, 604, 606 from the sequence 600 of test images includes plural test symbols 608. The person undergoing the test is required to activate the control 108 (ref. FIG. 1) in response to recognising test symbols in the set of test symbols 608 that replicate the shape of a target test symbol 610. In this case, the target symbol 610 is identified to the person throughout the duration of the sequence 600.

As depicted, in this example each of the test symbols 508 has a particular size from a predetermined range of sizes $s_k$ (where k=1 . . . n). Each size in the predetermined range of sizes has a predetermined relationship with a vision metric.

The size of the test symbols replicating the target symbol varies throughout the test so that any one of the test symbols replicating the shape of the target symbol will have a different size to at least some of the other test symbols replicating the shape of the target symbol.

In the depicted example, the sequence 600 of test images 602, 604, 606 is arranged so that the test symbols 608 appear to move from the right side of the display to the left side of the display over the sequence. However, in other embodiments the test symbols 608 may be static.

During the test, each test image 602, 604, 606 displays a set of test symbols 608 of different sizes to the person. The person activates the control 108 (ref. FIG. 1) on recognising a test symbol, or test symbols, that replicate the shape of the target symbol 610.

In the illustrated example, the activation of the control entails "shooting" the test symbol that the person recognises as replicating the shape of the test symbol. During the test, activation information for correct activations is obtained by the processor 106. In the present case, the activation information includes an activation ratio derived from counter values that, for each size, are indicative of number of test symbols displayed during the test that replicated the target symbol and the number of instances that the person correctly identified each size.

In the present example, the activation information is stored in memory on-board (or accessible) to the processor 106 in the form of respective arrays containing values that are updated during the test. For example, a first array contains a counter array ($c_1, c_2, c_3, c_4 \ldots c_n$) containing, for each size, a counter value that is indicative of the number of instances that the person correctly activated the controller, a second array ($d_1, d_2, d_3, d_4 \ldots d_n$) containing counter values that are indicative of the number of instances each test symbol size was displayed.

At the completion of the test, the activation information is processed to obtain a parameter value associated with the activations. In the present example, the activation information is the smallest angular size for which the person is able to reliably recognise test symbols as replicating the target symbol 610. More specifically, the activation information is the smallest angular size for which the person is able to recognise a replicated target symbol 610 with a correct activation ratio that exceeds 75%. In the illustrated example, the correct activation ratio (AR) is calculated as $AR_x = c_x/d_x$ (where x=1 . . . n). It will of course be appreciated that other values may be used for the 'correct activation ratio'.

In the present case, the test continues until sufficient activation information has been processed to identify the smallest angular size meeting the 75% ratio.

Having obtained the parameter value (which, in this case is a value of angular size), that value is then correlated with a vision metric so as to obtain a value for vision metric. Typically, the correlation will be performed by the processor 106, but it need not be since correlation could be performed manually using a suitable table or chart.

Figure 8:
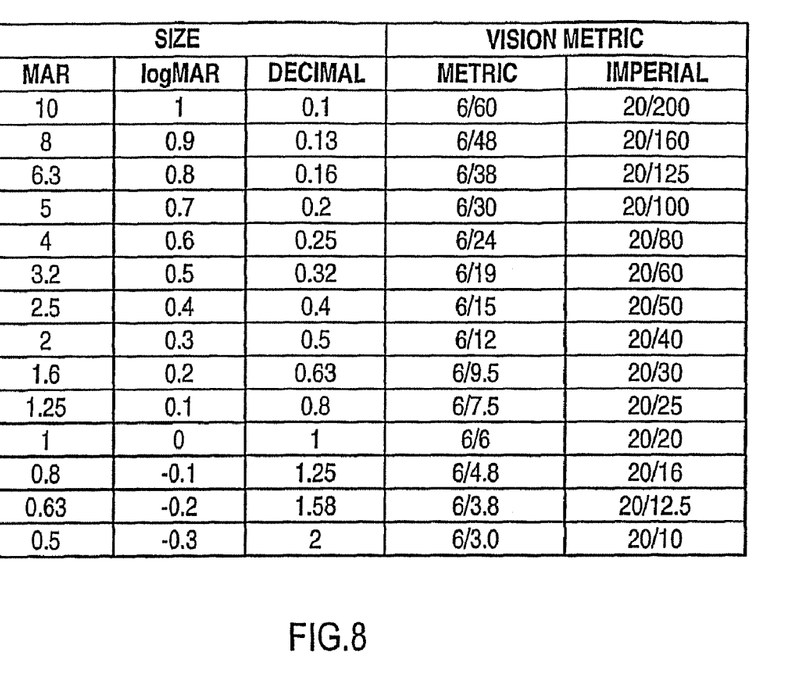
FIG. 8 is an example of scale of a predetermined relationship suitable for correlating a parameter with a vision metric.
Figure 9:
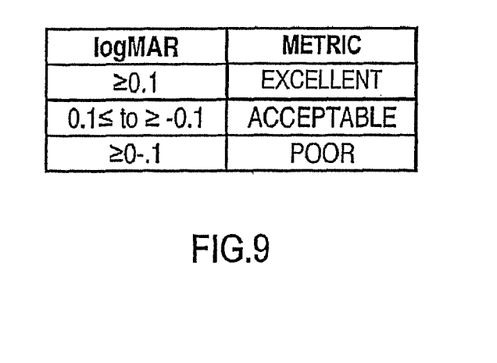
FIG. 9 is another example of scale of a predetermined relationship suitable for correlating a parameter with a vision metric.

In the present case, the obtaining a value for a metric of visual acuity involves retrieving, from a scale of values, a value having a predetermined relationship with the value of the average size. Two examples of suitable predetermined relationship are depicted in FIG. 8 and FIG. 9. As shown, FIG. 8 depicts a relationship between the value of the size parameter and a quantitative metric of visual acuity, whereas FIG. 9 depicts a relationship between the value of the size parameter and a qualitative metric of visual acuity. However, it will be appreciated that such a scale could also be used for other types of statistical values.

Figure 7:
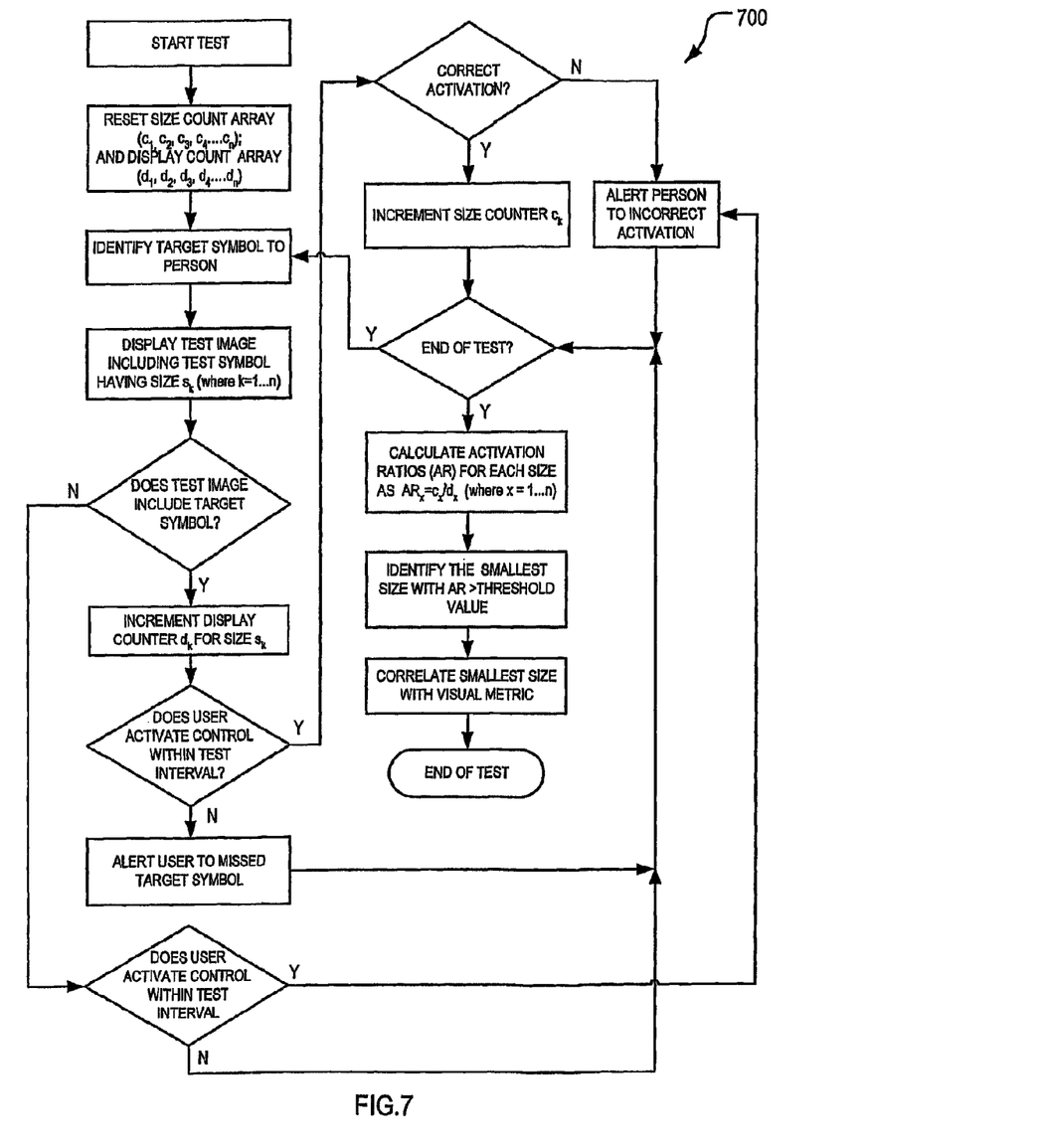
FIG. 7 is an example flow diagram for the method embodiment shown in FIG. 6.

Referring to FIG. 7 there is shown an example flow diagram 700 including the above-outlined steps.

Example 3

Figure 10:
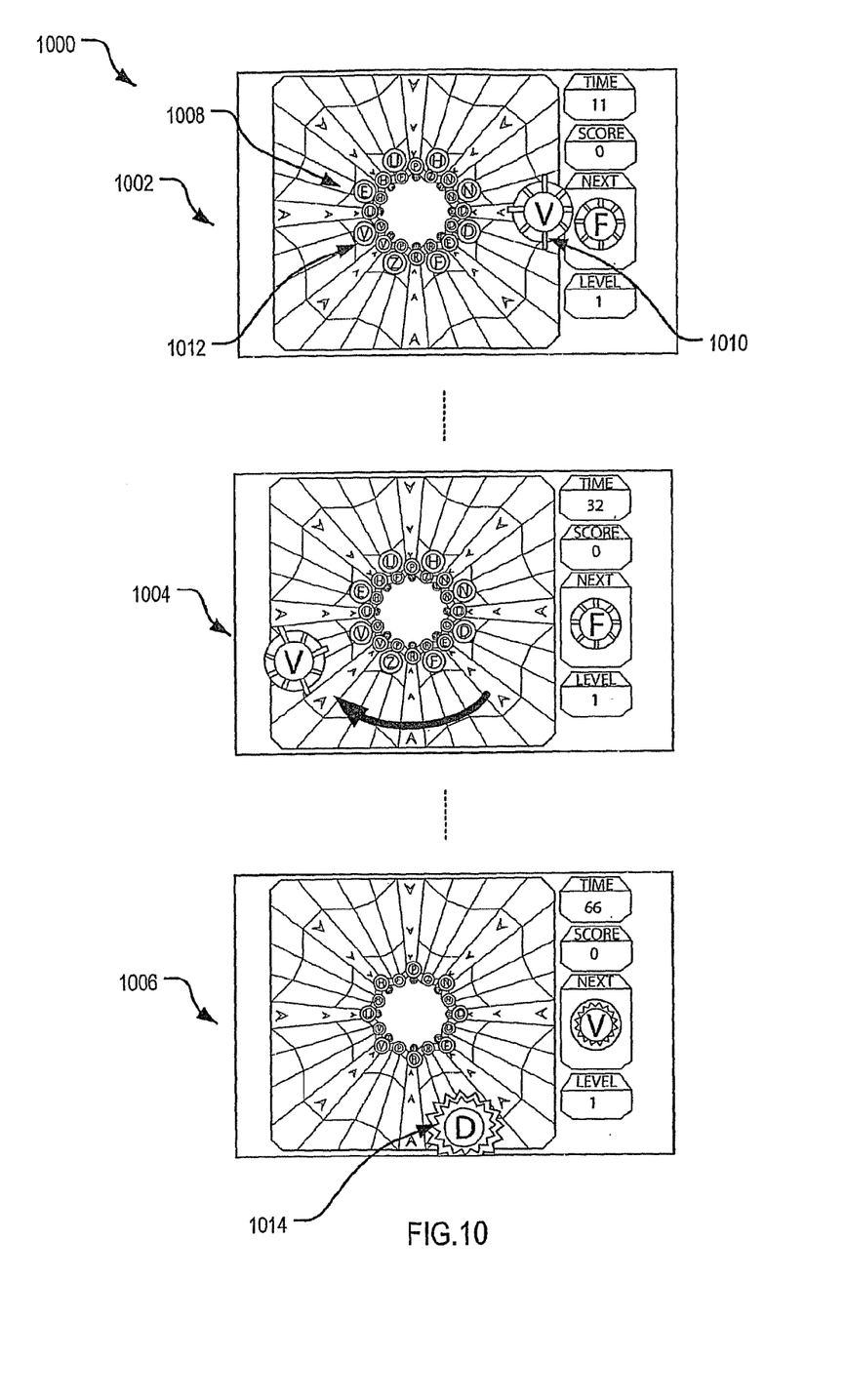
FIG. 10 is an example sequence of test images for a method in accordance with a third embodiment of the present invention.
Figure 11:
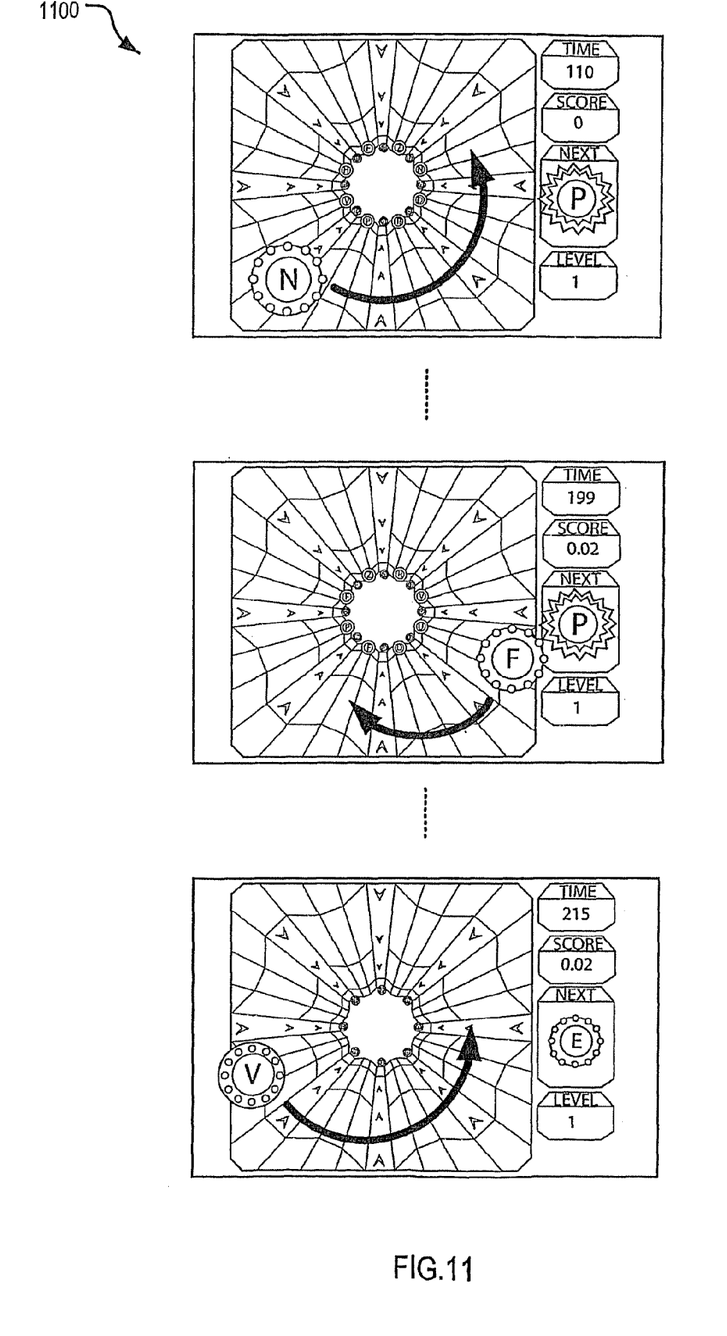
FIG. 11 is another example sequence of test images for the method embodiment shown in FIG. 10.

FIG. 10 and FIG. 11 depict example sequences of test images for a test method in accordance with a third embodiment of the present invention.

Turning initially to FIG. 10, there is shown a sequence 1000 including test images 1002, 1004, 1006. Each test image 1002, 1004, 1006 includes an arrangement of plural test symbols 1008. In the depicted arrangement includes plural sets of test symbols of equal angular size which, in the present case, are arranged as concentric rings. Each set includes test symbols having a size that is different to the size of the other sets.

During a test, the person is required to recognise, in a set-by-set manner, a test symbol from within each set that replicates the shape of a target symbol. In the present example the target symbol 1010 is displayed in each test image. In order to indicate recognition of a test symbol 1012, the person aligns the displayed target symbol 1010 with the test symbol replicating the target symbol and then activates the control 108 (ref. FIG. 1).

In the event that the person correctly recognises the test symbol 1012, the test continues with the person required to repeat the test for the next smallest set of test symbols.

As shown in the sequence 1100 depicted in FIG. 11, the above described process continues until the minimum activation ratio has been identified, corresponding with the set of test symbols having the smallest angular size that the person is able to reliably recognise.

An embodiment of the type depicted in FIG. 10 and FIG. 11 is particularly suitable for a "parametric estimation by sequential testing staircase type procedure". In such an embodiment, consecutive static test images adapt to the correct and incorrect activations by the person such that that the size of the next set of test symbols for activation is varied up and down relative to the previous set until a predefined correct threshold value (for example, 75%) is achieved, at which point the sequence is terminated.

The present invention may be implemented as a stand-alone or on-line version. An on-line version is expected to offer additional benefits as it may tend to attract persons to conduct a test of their own volition. An embodiment of the present invention that resembles a computer game is expected to particularly appeal to juvenile persons.

Finally, it will be understood that there may be other variations and modifications to the configurations described herein that are also within the scope of the present invention.

The invention claimed is:

1. A method of testing a person's vision, the method including:
   providing a computer game environment displaying one or more sequences of test images, each test image including one or more test symbols;
   for each test image, or for each sequence, identifying a target symbol to the person;
   providing a game control for activation during game play in response to the person viewing each test image in the sequence and recognizing a test symbol that replicates the shape of the target symbol;
   processing activation information associated with the activation of the game control to obtain a parameter value associated with the activations; and
   correlating the parameter value with a vision metric.

2. A method according to claim 1 wherein testing the person's vision includes testing one or more of:
   a. near vision acuity;
   b. distance vision acuity;
   c. contrast sensitivity;
   d. stereo-acuity;
   e. binocular function;
   f. peripheral vision performance; and
   g. colour vision.

3. A method according to claim 1 wherein the sequence of test images is displayed as one of:
   a. a sequence of dynamic test images;
   b. a sequence of static test images; or
   c. a combination of static and dynamic test images.

4. A method according to claim 1 wherein each test image includes one or more test symbols that progressively enlarge during a test interval.

5. A method according to claim 4 wherein not all of the test images include a test symbol that replicates the shape of the target symbol.

6. A method according to claim 1 wherein the activation information includes one or more of:
   (a) a response time for the activation; or
   (b) the angular size of the test symbol at the instant of activation.

7. A method according to claim 6 wherein processing the activation information to obtain a parameter value associated with the activations, includes processing the angular size of the test symbols for the activations and identifying a parameter value in the form of a minimum angular size for which correct activations were achieved at a threshold rate exceeding a minimum threshold value.

8. A method according to claim 7 wherein the minimum angular size is indexed into a scale of values of a visual metric having a predetermined relationship with the range of an angular size values so as to obtain the value of the visual metric for the minimum angular size.

9. A method according to claim 1 wherein for consecutive test images, the size of the test symbol replicating the shape of the target symbol is modified in accordance with the activation information for the preceding test image in the consecutive test images, so that if that activation information was indicative of a correct activation then the size of the test symbol in the later test image in the consecutive sequence is decreased, or if that earlier activation information was indicative of a incorrect activation then the size of the test symbol replicating the target symbol in the next test image is increased.

10. A method according to claim 9 wherein modification of the size of the test symbol continues iteratively until a minimum angular size for which the wearer is able to correctly recognized a test symbol replicating the target symbol at a minimum threshold rate has been determined.

11. A method according to claim 1 wherein the sequence of test images is displayed as one of:
   a. a sequence of dynamic test images;
   b. a sequence of static test images; or
   c. a combination of static and dynamic test images.

12. A method according to claim 1 wherein each test image includes one or more test symbols that progressively enlarge during a test interval.

13. A method according to claim 12 wherein not all of the test images include a test symbol that replicates the shape of the target symbol.

14. A method according to claim 1 wherein the activation triggers a game response.

15. A method of testing a person's vision, the method including:
   providing a computer game environment displaying a dynamic graphical image including a symbol that progressively enlarges during a test interval, the symbol enlarging from a size at which the symbol is unrecognizable to the person to a size at which the symbol is recognizable to the person;
   providing a game control for activation during game play by the person at the instant, during the test interval, that the person recognizes the symbol; and
   correlating the activation of the game control with a vision metric.

16. A method according to claim 15 wherein the activation triggers a game response.

17. An interactive system for testing the vision of a person, the system including:
   a graphics display device;
   a graphics processor for providing a computer game environment for displaying on the graphics device, the computer game environment including a sequence of test images, each test image including one or more test symbols;
   an identifying means for identifying, for each test image or sequence, a target symbol to the person;
   a game controller for activation during game play by the person viewing each test image in the sequence in response to recognizing a test symbol that replicates the shape of the target symbol;

a processor for processing activation information to obtain a parameter value associated with the activations for correlating with a vision metric;

wherein processing the activation information to obtain a parameter value associated with the activations, includes processing the angular size of the test symbols for the activations and identifying a parameter value in the for of a minimum angular size for which correct activations were achieved at a threshold rate exceeding a minimum threshold value.

18. An interactive system according to claim 17 wherein the activation triggers a game response.

19. A system for testing a person's vision, the system including processor and associated memory device for storing a series of instructions to cause the processor to:
display a computer game environment including one or more sequences of test images, each test imagine including one or more test symbols;
for each test image, or for each sequence, identify a target symbol to the person; and
processing activation information to obtain a parameter value associated with the activations for correlation with a vision metric;
wherein the activation information is associated with activations of a game control during game play by a person viewing each test image in the sequence, and wherein each activation is in response to the person recognizing a test symbol that replicates the shape of the target symbol.

20. A system according to claim 19 wherein the activation triggers a game response.

21. Computer software for use in a system testing a person's vision, the system including a processor and associated memory device for storing the computer software including a series of instructions to cause the processor to:
display, on a graphical display, a computer game environment including one or more sequences of test images, each test image including one or more test symbols;
for each test image, or for each sequence, identify a target symbol to the person; and
processing activation information to obtain a parameter value associated with the activations for correlation with a vision metric;
wherein the activation information is associated with activations of a game control during game play by a person viewing each test image in the sequence, and wherein each activation is in response to the person recognizing a test symbol that replicates the shape of the target symbol.

22. Computer software according to claim 21 wherein the activation triggers a game response.

* * * * *